US012204125B2

(12) United States Patent
Jacobson et al.

(10) Patent No.: US 12,204,125 B2
(45) Date of Patent: Jan. 21, 2025

(54) OPTICAL FILTER DEVICE, SYSTEM, AND METHODS FOR IMPROVED OPTICAL REJECTION OF HIGH ANGLE OF INCIDENCE (AOI) LIGHT

(71) Applicant: Profusa, Inc., Emeryville, CA (US)

(72) Inventors: Benjamin Jacobson, Richmond, CA (US); Gregory Kintz, Emeryville, CA (US)

(73) Assignee: Profusa, Inc., Emeryville, CA (US)

( * ) Notice: Subject to any disclaimer, the term of this patent is extended or adjusted under 35 U.S.C. 154(b) by 327 days.

(21) Appl. No.: 17/179,800

(22) Filed: Feb. 19, 2021

(65) Prior Publication Data

US 2021/0255378 A1   Aug. 19, 2021

Related U.S. Application Data

(60) Provisional application No. 62/978,673, filed on Feb. 19, 2020.

(51) Int. Cl.
*G02B 5/28* (2006.01)
*G02B 5/22* (2006.01)
*G02B 5/26* (2006.01)

(52) U.S. Cl.
CPC ............. *G02B 5/288* (2013.01); *G02B 5/22* (2013.01); *G02B 5/26* (2013.01)

(58) Field of Classification Search
CPC . G02B 5/288; G02B 5/22; G02B 5/26; G02B 6/12007; G02B 2006/02166;
(Continued)

(56) References Cited

U.S. PATENT DOCUMENTS 6,978,057 B1 * 12/2005 O'Gorman ............ H01S 5/4031
385/37
7,045,052 B2    5/2006 Kochergin et al.
(Continued)

FOREIGN PATENT DOCUMENTS

EP    2434319 A2    3/2012
EP    3003131 A2    4/2016
(Continued)

OTHER PUBLICATIONS

English translation for JP-2002321935-A, Hasegawa (Year: 2002).*
(Continued)

*Primary Examiner* — Jonathan Y Jung
(74) *Attorney, Agent, or Firm* — COOLEY LLP

(57) ABSTRACT

An optical filter device, system, and methods for improved optical rejection of high angle of incidence (AOI) light is disclosed. For example, an analyte detection system is provided that includes an excitation light source for illuminating an implantable sensor and an optical detector for collecting emission light from the implantable sensor. Further, the optical detector portion of the analyte detection system features an optical filter device including a surface-treated microchannel wherein the surface-treated microchannel serves to absorb, trap, and/or block high-AOI light. Further, a method of operation of the presently disclosed microchannel-based optical filter device including a surface-treated microchannel is provided with respect to the high optical rejection of high-AOI light.

9 Claims, 19 Drawing Sheets

(58) Field of Classification Search
CPC ........ A61B 2562/0233; G01N 21/0303; G02F 1/0151; G02F 2201/307
See application file for complete search history.

(56) References Cited

U.S. PATENT DOCUMENTS

| | | | |
|---|---|---|---|
| 7,194,174 B2 | 3/2007 | Dridi et al. | |
| 2004/0134879 A1* | 7/2004 | Kochergin | G02B 6/1225 |
| | | | 216/24 |
| 2011/0013269 A1* | 1/2011 | Ogawa | G02B 6/122 |
| | | | 359/341.1 |
| 2019/0056591 A1* | 2/2019 | Tervo | G02B 6/0038 |
| 2020/0008719 A1* | 1/2020 | Bremer | A61B 5/14551 |

FOREIGN PATENT DOCUMENTS

| | | | | |
|---|---|---|---|---|
| JP | 2002321935 A | * | 11/2002 | ....... C03B 37/01205 |
| WO | WO-2011000622 A1 | | 1/2011 | |
| WO | WO-2013163298 A1 | | 10/2013 | |
| WO | WO-2019039371 A1 | | 2/2019 | |

OTHER PUBLICATIONS

International Preliminary Report on Patentability for International Application No. PCT/US2021/018725, mailed on Sep. 1, 2022, 12 pages.
International Search Report and Written Opinion for International Application No. PCT/US2021/018725 dated Jun. 9, 2021, 16 pages.
Luan F., et al., "All-Solid Photonic Bandgap Fiber," Optics Letters. Optical Society of America, Oct. 2004, vol. 29(20), pp. 2369-2371.
Pacholski C., "Photonic CrystalSensors Based on Porous Silicon," Sensors, Apr. 2013, vol. 13(4), pp. 4694-4713.
Russell P., "Photonic Crystal Fibers," Science. American Association for the Advancement of Science, Jan. 2003, vol. 299, pp. 358-362.
Suzuki K., et al., "Three-Dimensional Photonic Crystals Created by Single-Step Multi- Directional Plasma Etching," Optics Express, Jul. 2014, vol. 22(14), pp. 17099-17106.

* cited by examiner

Microchannel-etched wafer 200

OPTICAL FILTER DEVICE, SYSTEM, AND METHODS FOR IMPROVED OPTICAL REJECTION OF HIGH ANGLE OF INCIDENCE (AOI) LIGHT

CROSS REFERENCE TO RELATED APPLICATIONS

This application claims priority to U.S. Provisional Application No. 62/978,673, filed Feb. 19, 2020, the entire disclosure of which is hereby incorporated by reference.

TECHNICAL FIELD

The presently disclosed subject matter relates generally to optical band-pass filters and more particularly to an optical filter device, system, and methods for improved optical rejection of high angle of incidence (AOI) light.

BACKGROUND

In the management of many medical and/or health conditions, it can be desirable to regularly measure of analytes in vivo. For example, measurement of glucose in the blood can be useful to ensure correct insulin dosing in diabetic patients. Furthermore, it has been demonstrated that in the long-term care of the diabetic patient better control of the blood glucose levels can delay, if not prevent, the onset of retinopathy, circulatory problems and other degenerative diseases often associated with diabetes.

Currently, biosensors exist that can be implanted in tissue. For example, biosensors exist that can be implanted a few millimeters under the skin. In such sensors, luminescent dyes are used to measure the concentration of an analyte of interest (e.g., oxygen, glucose, lactate, carbon dioxide ($CO_2$), pH). For example, the intensity of a certain luminescent dye can modulate based on the amount of analyte present, wherein the intensity of the emission light can be correlated to the analyte concentration. However, intensity-based systems can be challenging because the detector (or reader) is subject to potential sources of error and noise that make it difficult to get an accurate analyte measurement.

For example, the optical power reflected or elastically scattered by the skin from a fluorophore excitation source is often orders of magnitude stronger than the resulting fluorescence emission. Using an optical filter to separate the excitation light from the emission light has certain challenges. For example, the cutoff wavelengths (or filter window) for optical band-pass filters are dependent on the angle of incidence (AOI) of the incident light. AOI is defined as the angle between an incident ray and the filter surface normal at the point of incidence. As AOI increases, the filter window shifts to shorter wavelengths (i.e., blue shifts). In the case of fluorophore excitation and emission, this blue shift causes the optical filter window for the emission to shift towards the excitation light source. Accordingly, when relying on intensity-based measurements, a challenge exists for providing an optical filter that can reject elastically scattered excitation light at orders of magnitude greater than emission light power at the worst-case AOI of the system.

BRIEF DESCRIPTION OF THE DRAWINGS

Figure 1:
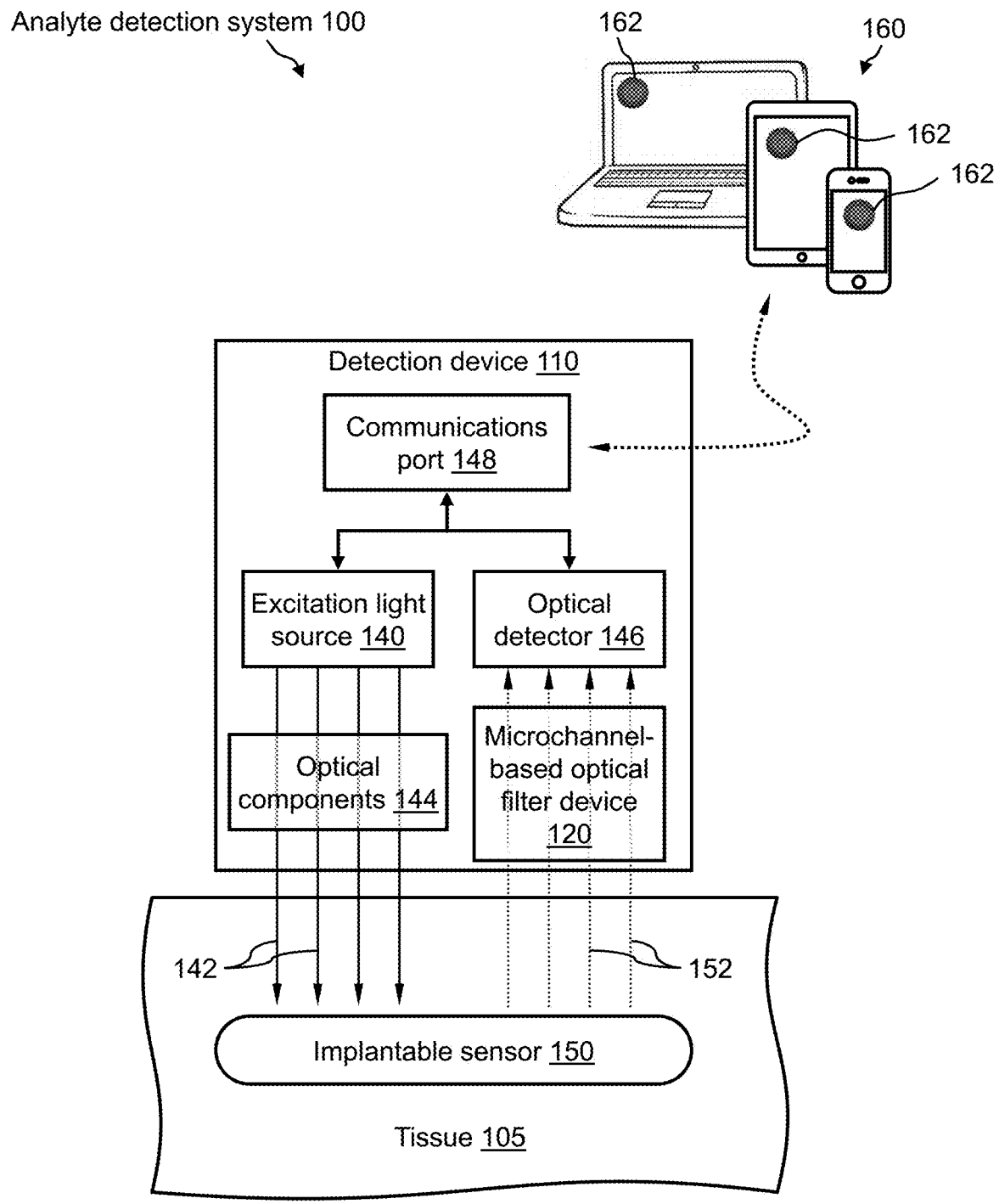
Figure 2:
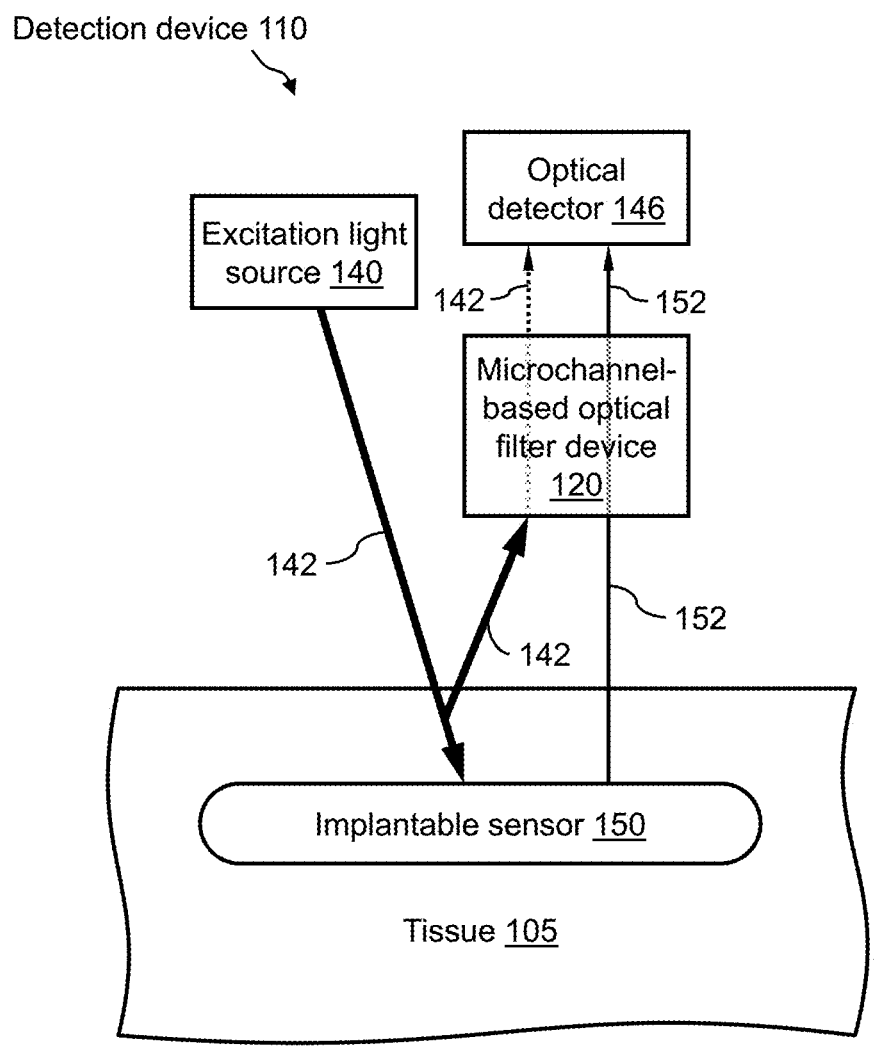
Figure 3:
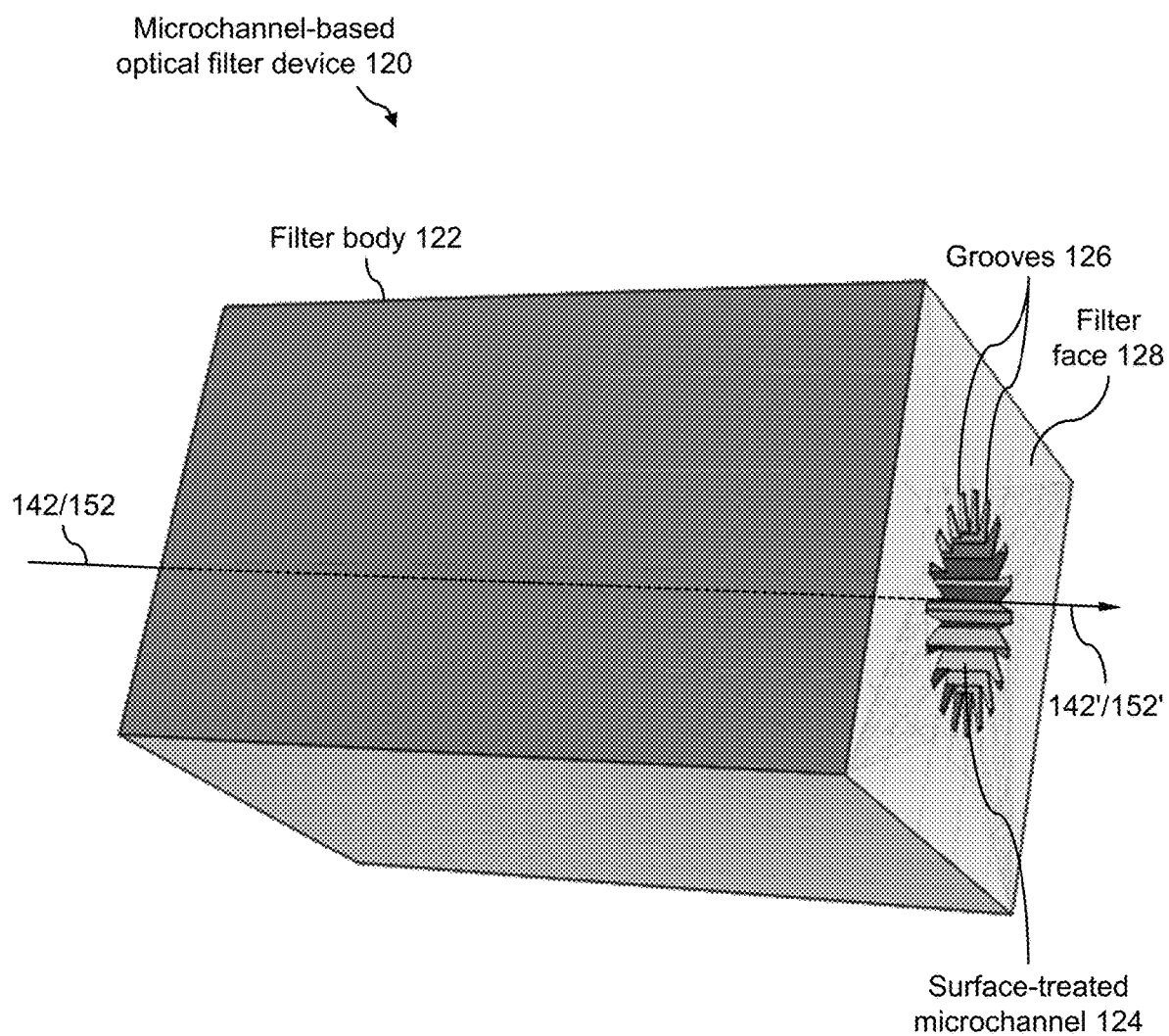
Figure 4A:
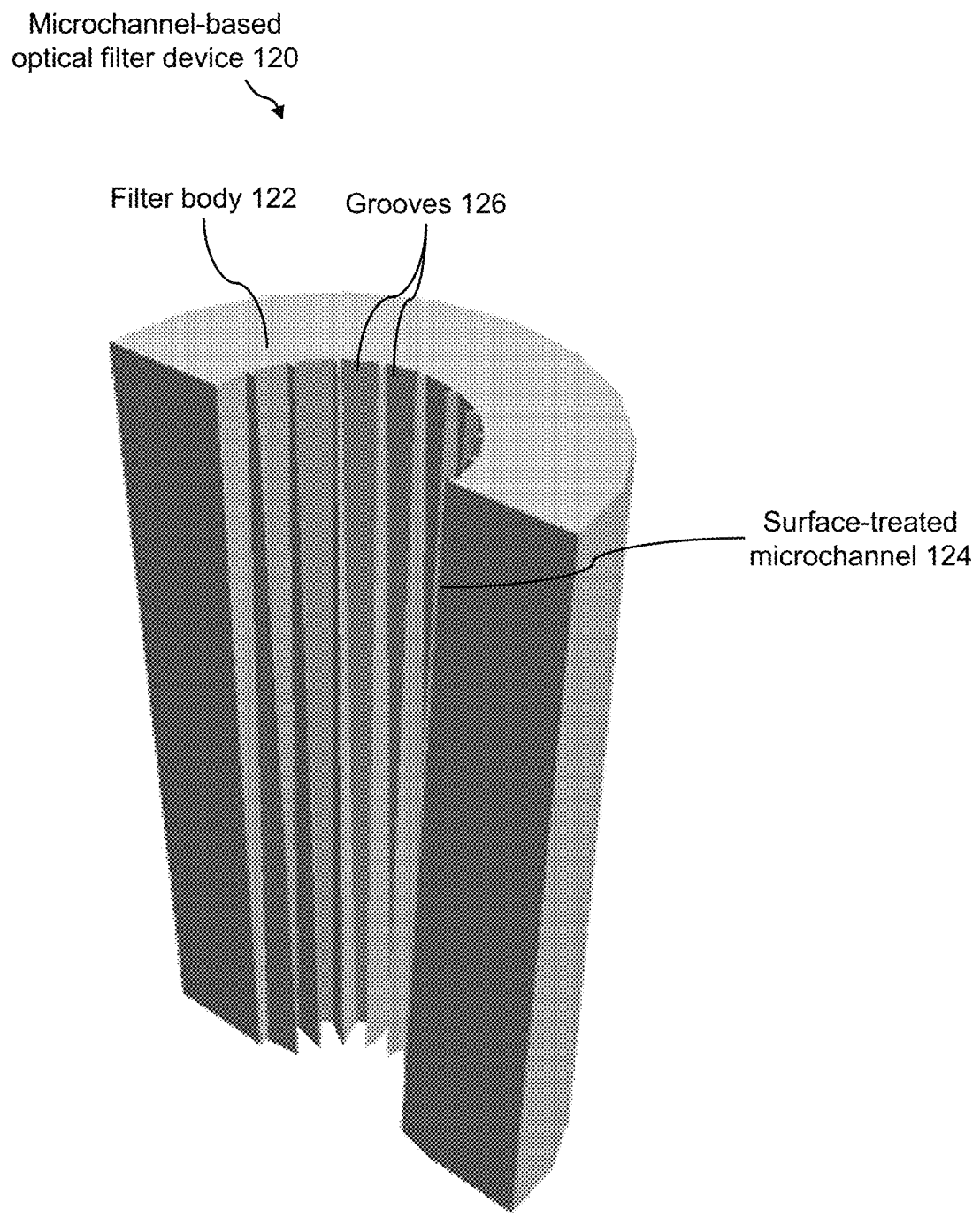
Figure 4B:
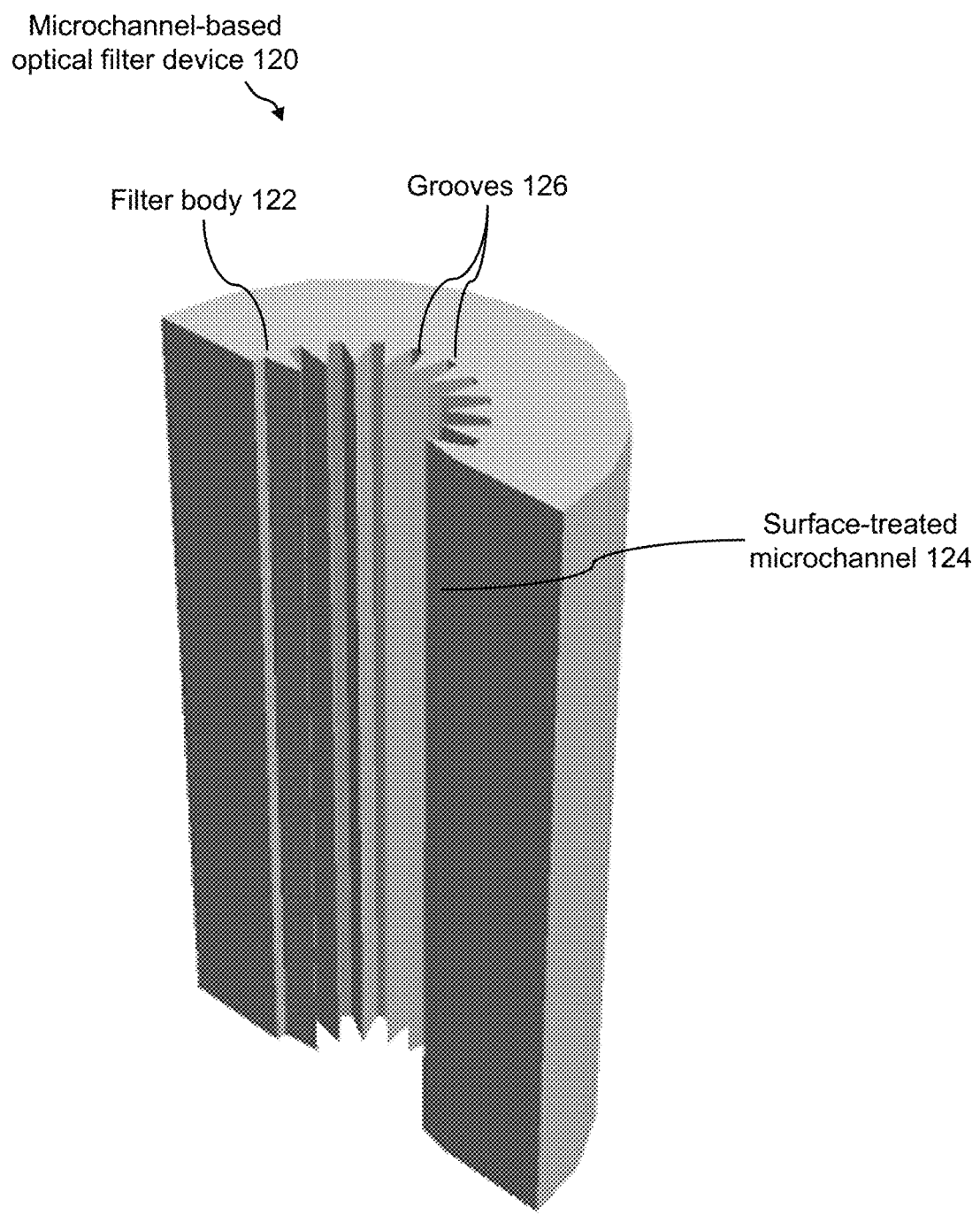
Figure 5:
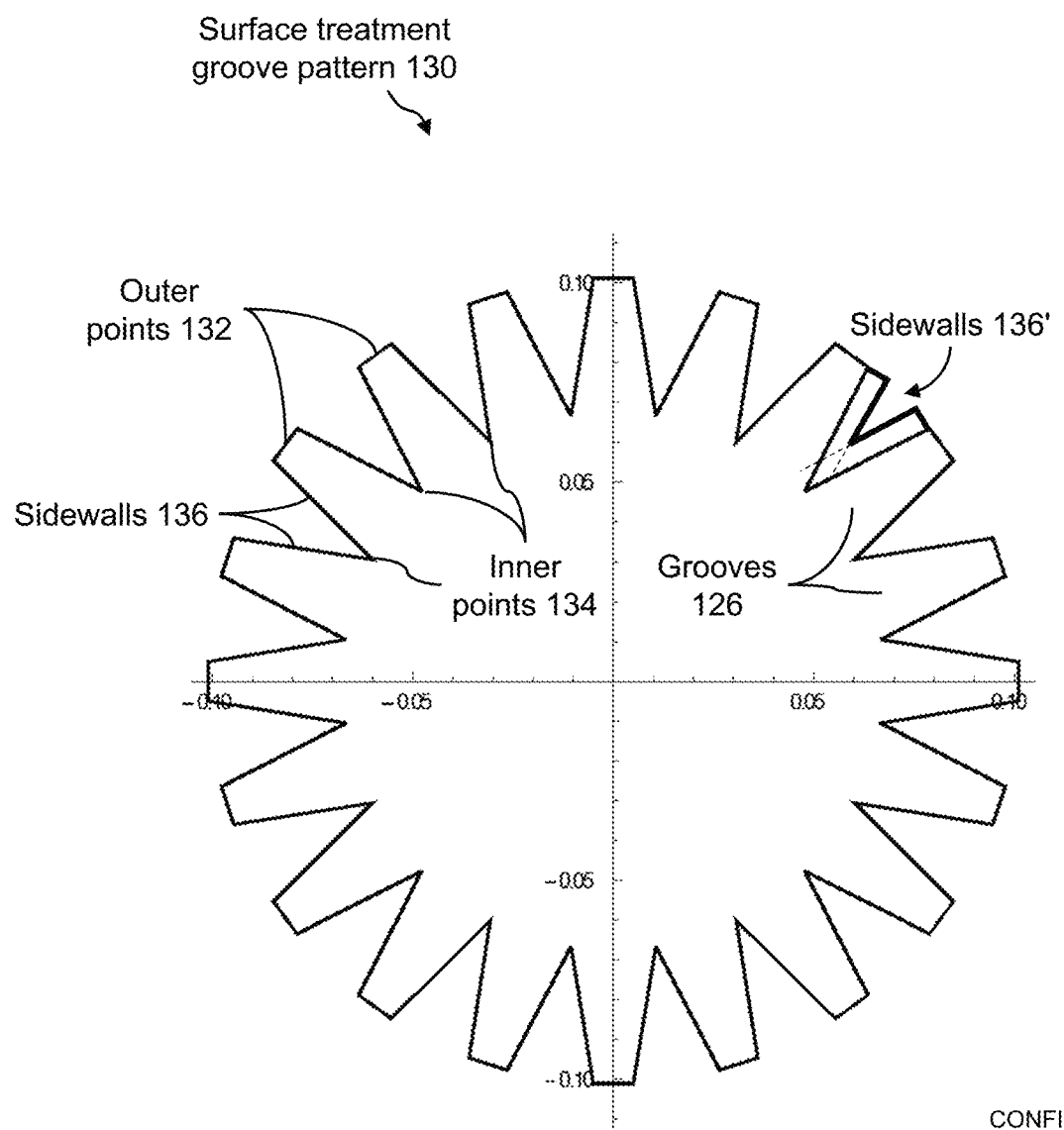
Figure 6:
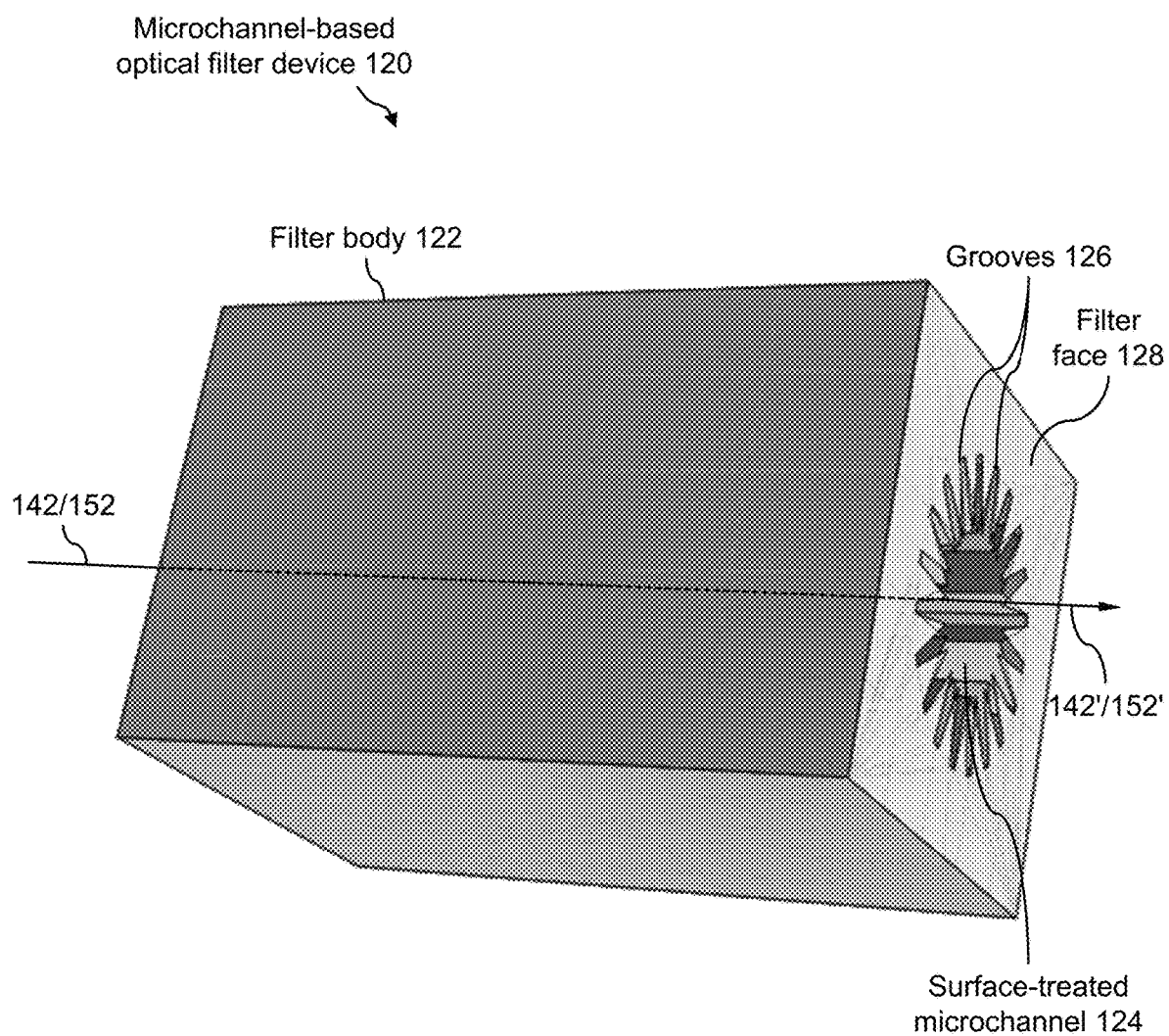
Figure 7:
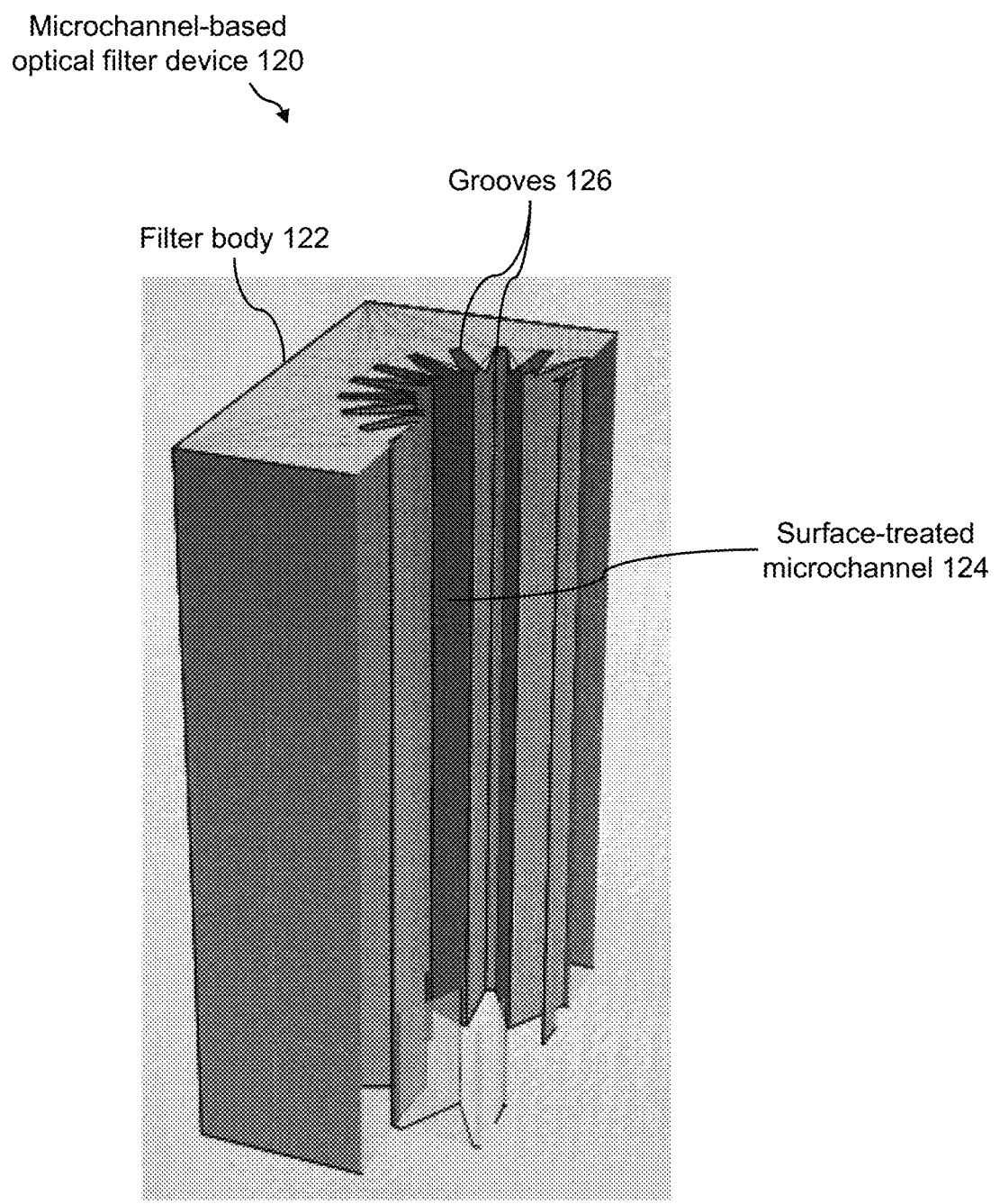
Figure 8:
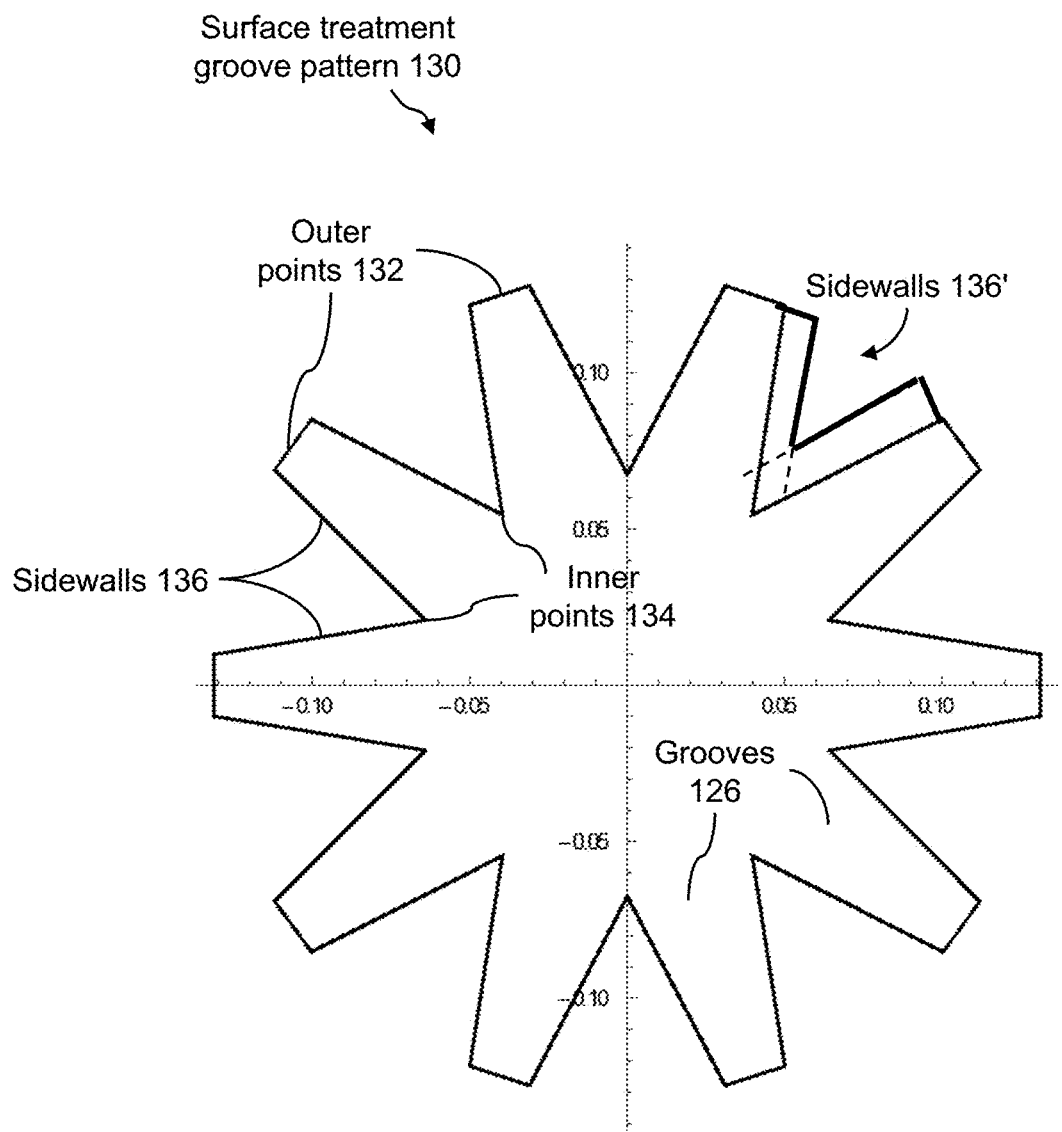
Figure 9:
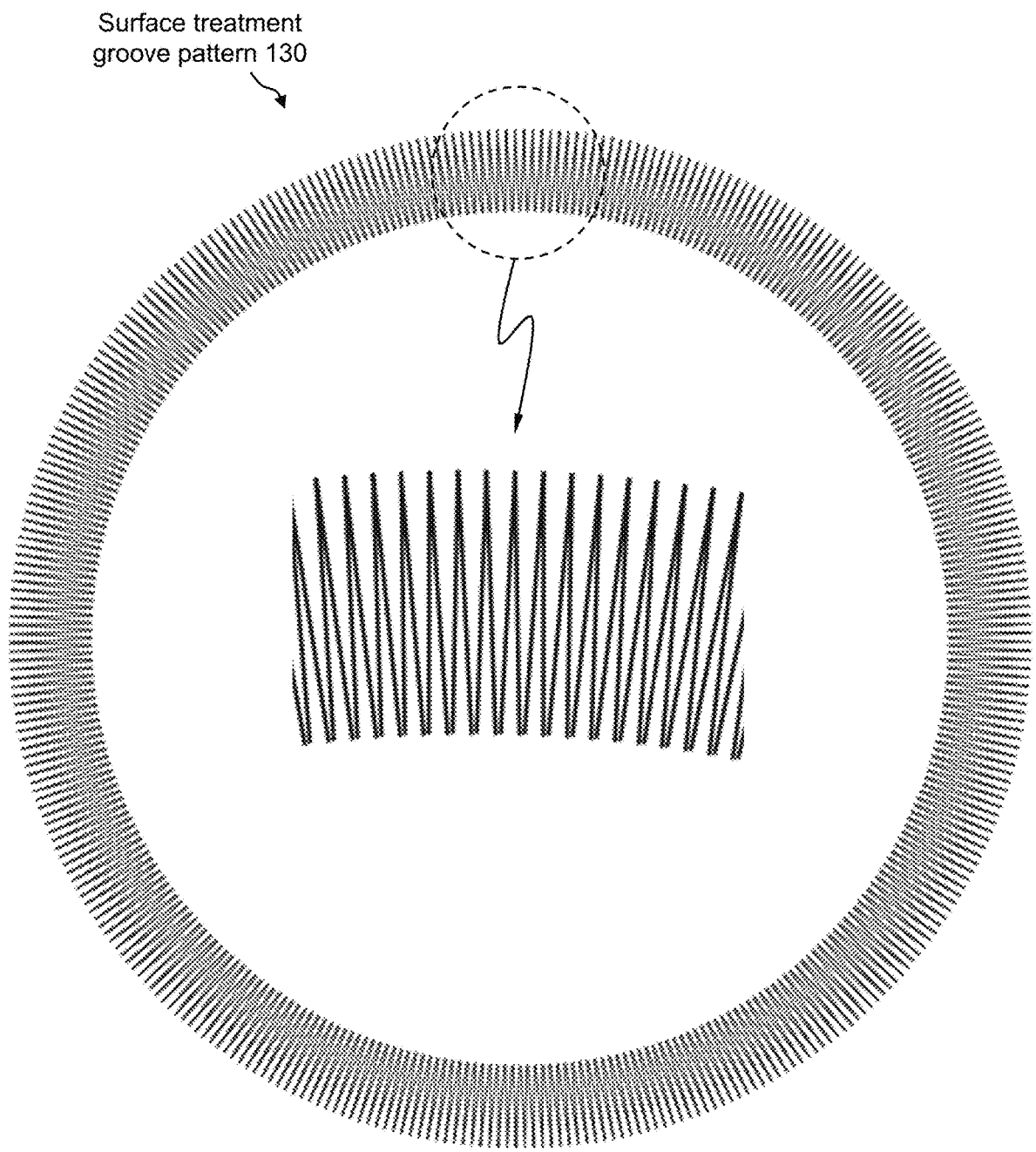
Figure 10:
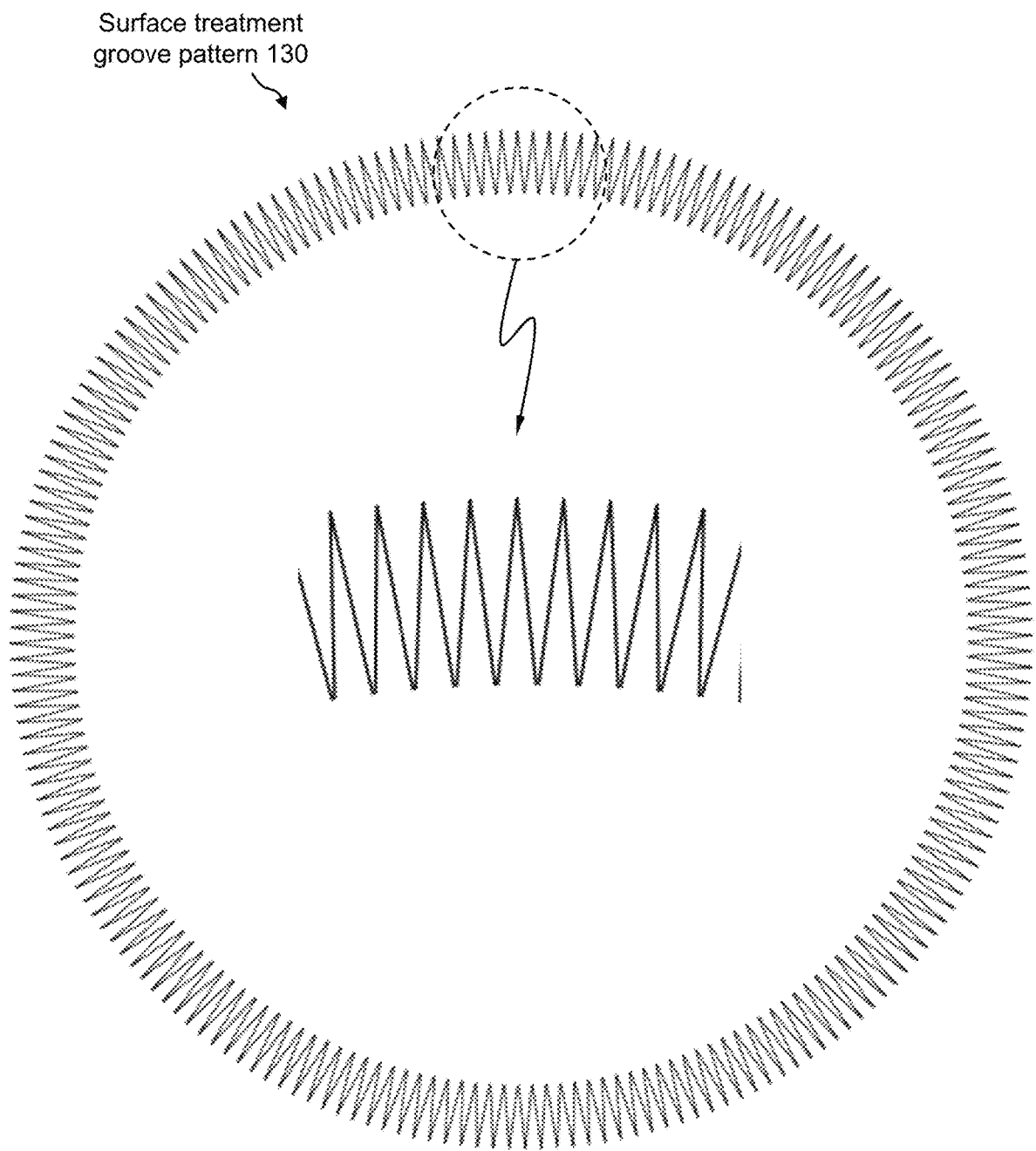
Figure 11:
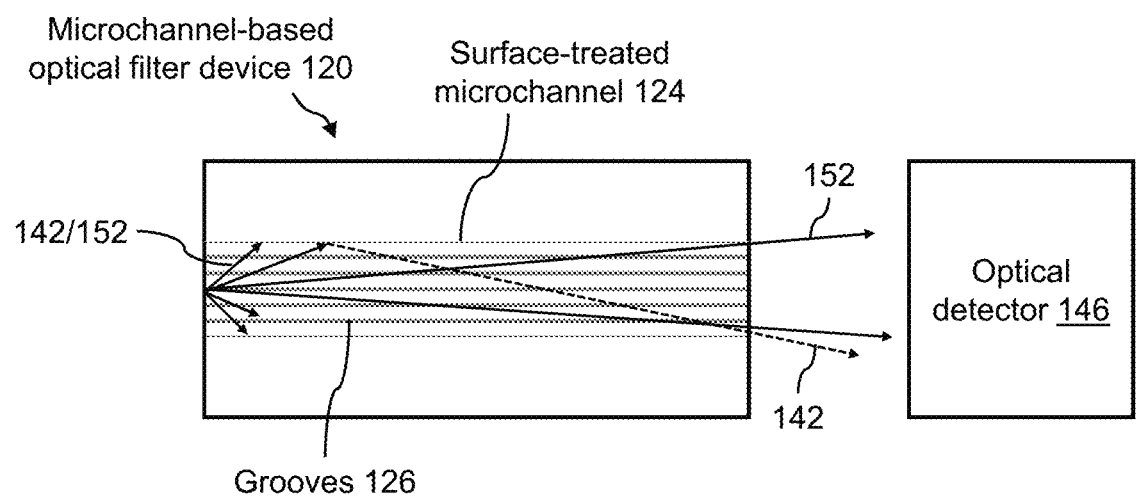
Figure 12:
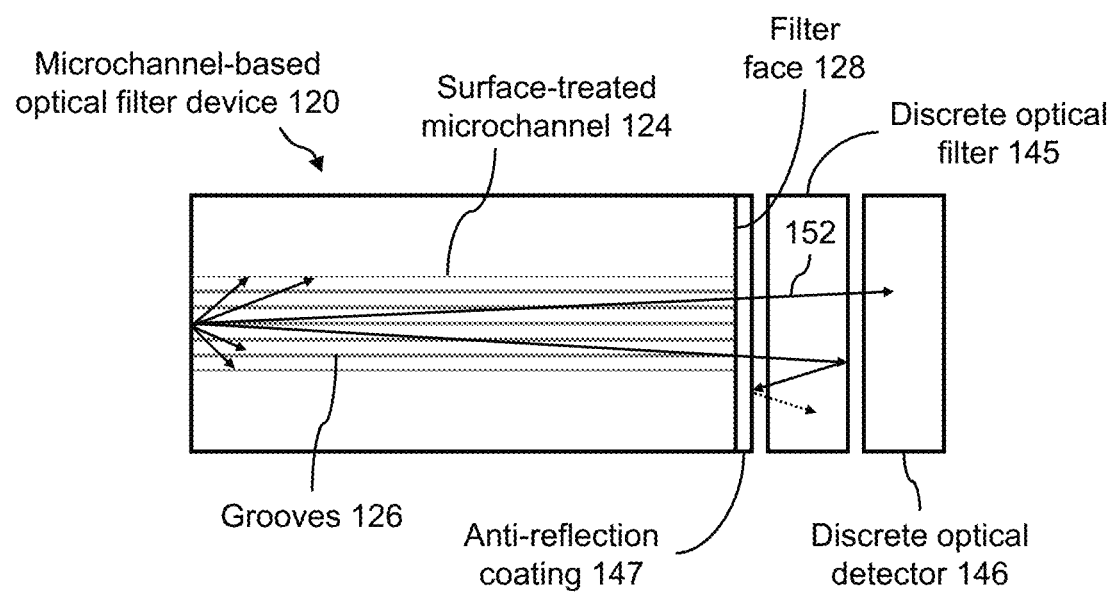
Figure 13:
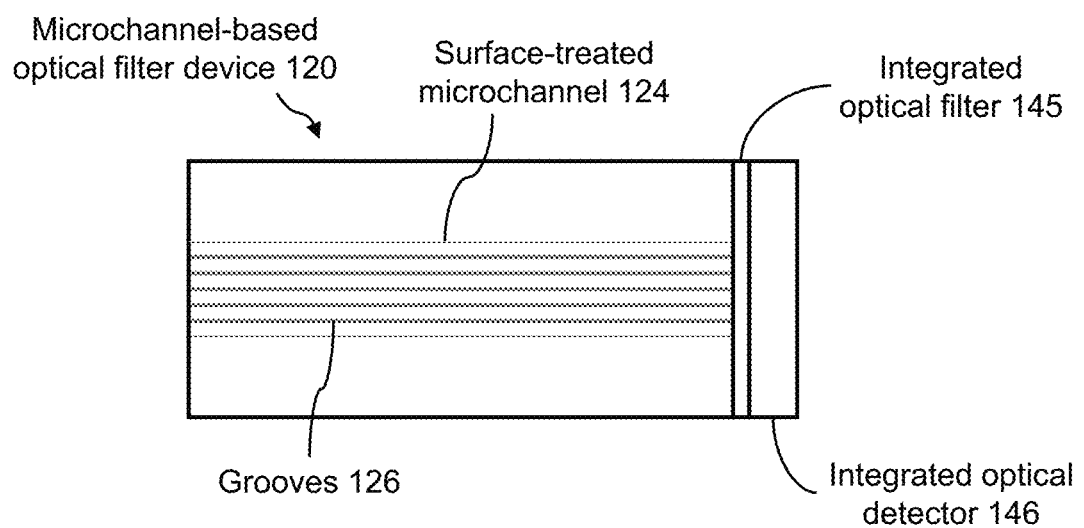
Figure 14:
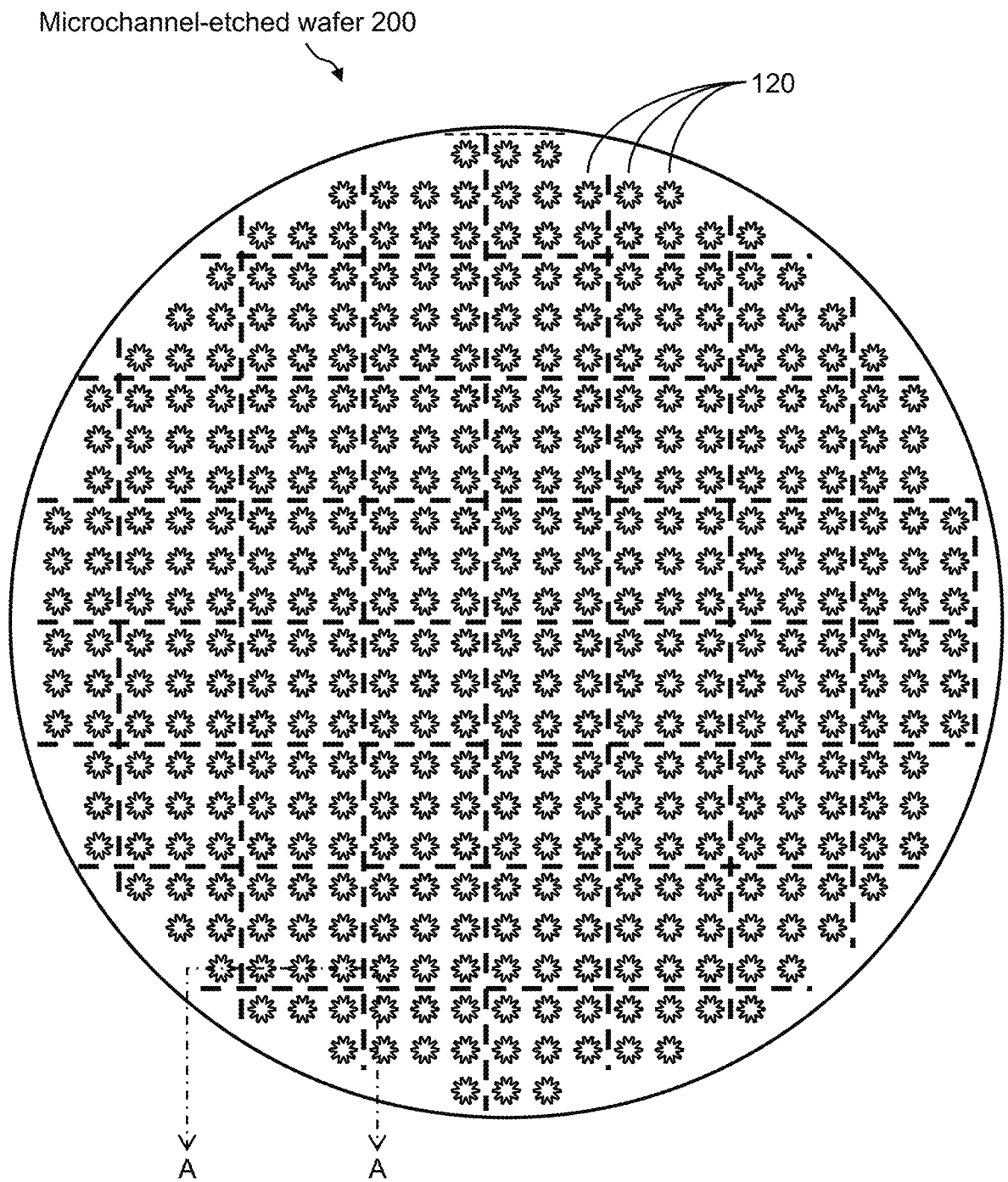
Figure 15:
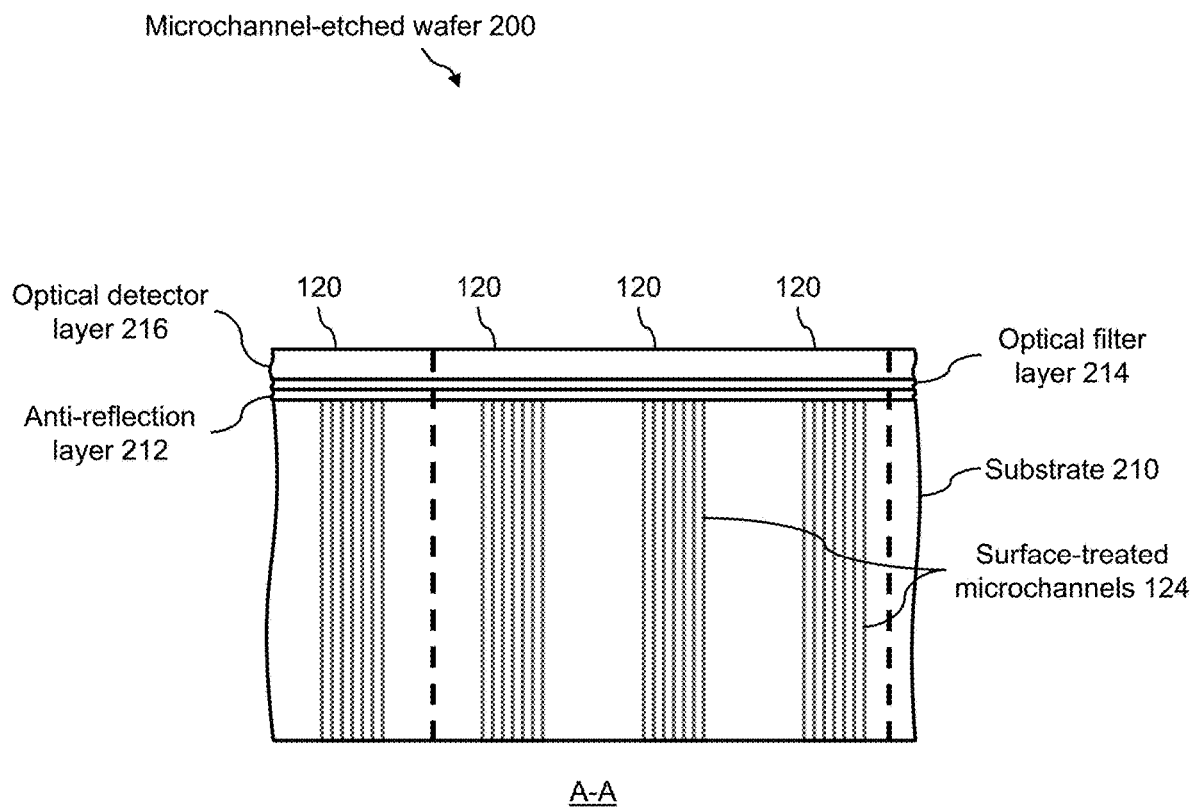
Figure 16:
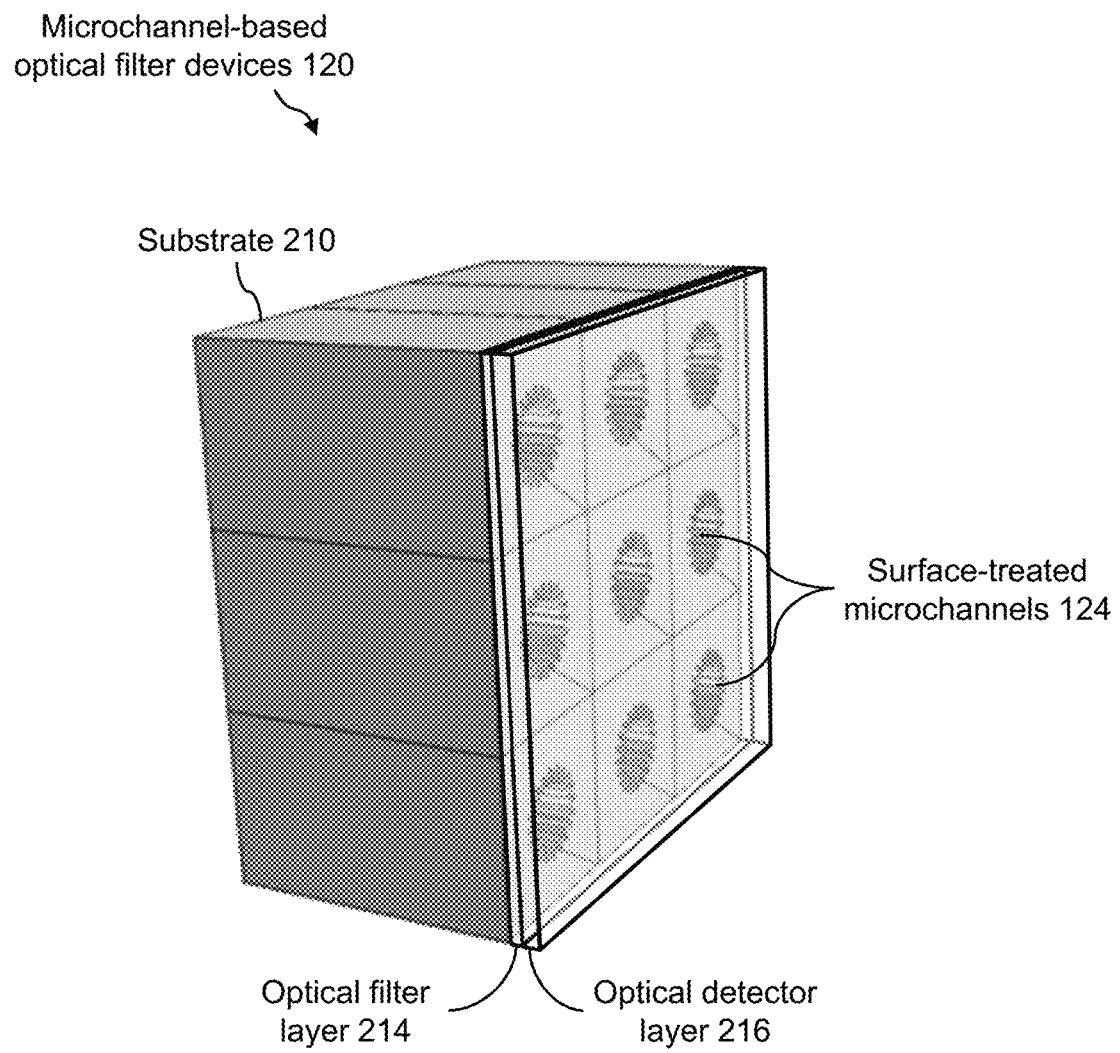
Figure 17:
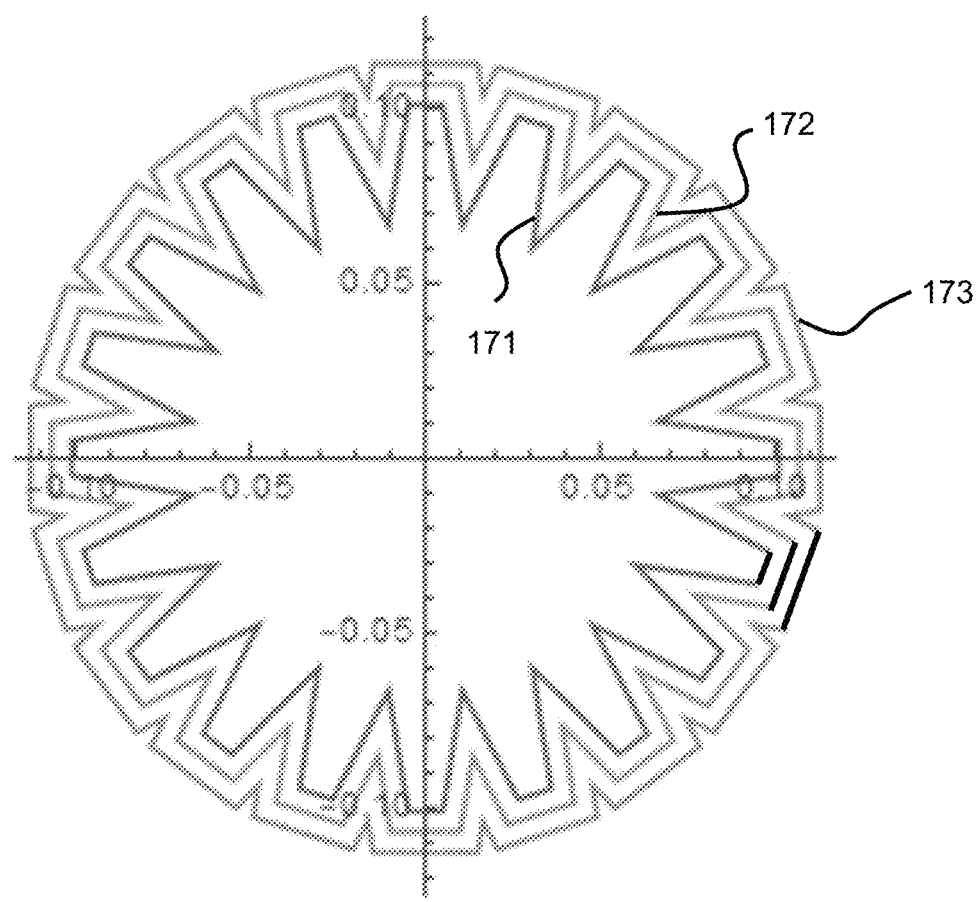
Figure 18:
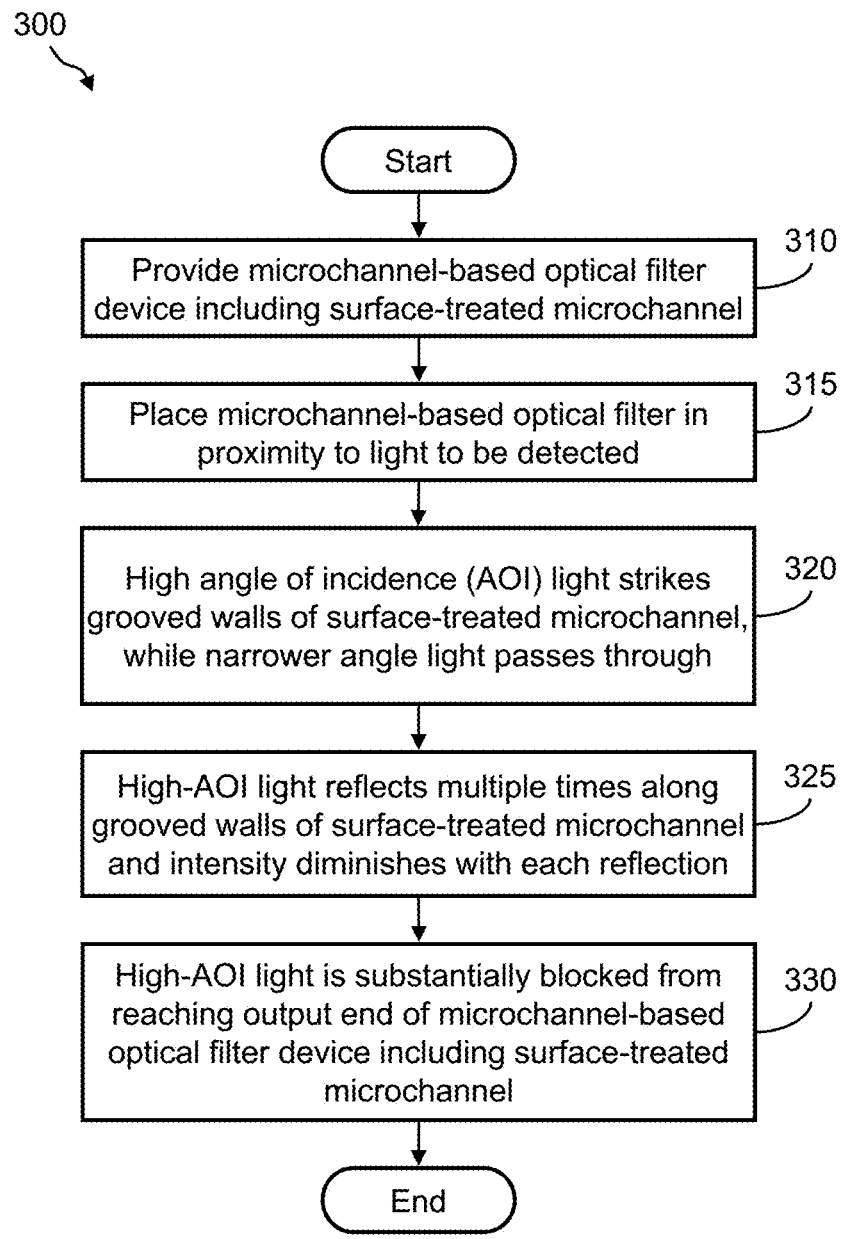

Having thus described the presently disclosed subject matter in general terms, reference will now be made to the accompanying drawings, which are not necessarily drawn to scale, and wherein:

FIG. 1 illustrates a block diagram of an example of the presently disclosed analyte detection system including a microchannel-based optical filter device providing high optical rejection of high-AOI light;

FIG. 2 illustrates a block diagram of an example of the microchannel-based optical filter device portion of the presently disclosed analyte detection system;

FIG. 3 illustrates a full perspective view and FIG. 4A and FIG. 4B illustrate a cutaway perspective view of examples of a microchannel-based optical filter device including a surface-treated microchannel; FIG. 4A illustrates tapering of the microchannels, and FIG. 4B illustrates zero-tapering;

FIG. 5 illustrates a plan view of an example of a surface treatment groove pattern for forming the surface-treated microchannel of the microchannel-based optical filter device shown in FIG. 3, FIG. 4A, and FIG. 4B;

FIG. 6 and FIG. 7 illustrate a full perspective view and a cutaway perspective view, respectively, of another example of a microchannel-based optical filter device including a surface-treated microchannel;

FIG. 8 illustrates a plan view of an example of a surface treatment groove pattern for forming the surface-treated microchannel of the microchannel-based optical filter device;

FIG. 9 and FIG. 10 illustrate yet other examples of surface treatment groove patterns for forming the surface-treated microchannel of the microchannel-based optical filter device;

FIG. 11 illustrates a block diagram of an example of the microchannel-based optical filter device according to a configuration;

FIG. 12 illustrates a block diagram of another example of the microchannel-based optical filter device including other discrete optical components;

FIG. 13 illustrates a block diagram of an example of an integrated microchannel-based optical filter device including other integrated optical components;

FIG. 14 illustrates a plan view of an example of a microchannel-etched wafer for supporting the large-scale manufacturing process of the microchannel-based optical filter devices;

FIG. 15 illustrates a cross-sectional view of a portion of the microchannel-etched wafer shown in FIG. 14;

FIG. 16 illustrates a perspective view of a block of the microchannel-based optical filter devices that may be diced from the microchannel-etched wafer shown in FIG. 14 and FIG. 15;

FIG. 17 illustrates a series of cross-sections at different etching depths of an example of a surface-treated microchannel model and indicating the etching characteristics thereof; and FIG. 18 illustrates a flow diagram of an example of a method of operation of the microchannel-based optical filter device of the presently disclosed analyte detection system.

DETAILED DESCRIPTION

The presently disclosed subject matter now will be described more fully hereinafter with reference to the accompanying drawings. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides an optical filter device, system, and methods for improved optical rejection of high-AOI light. For example, an analyte detection system is provided that includes an excitation light source for illuminating an implantable sensor and an optical detector for collecting emission light from the implantable sensor. Further, the optical detector portion of the analyte detection system features an optical filter device including a surface-treated microchannel wherein the surface-treated microchannel serves to absorb, trap, and/or block high-AOI light. For our purposes a "filter" can be generally defined has a device that receives an input light flux having a distribution of angles, positions, wavelengths, and polarization states, and outputs an output light flux having a different distribution of angles, positions, wavelengths, and polarization states. From this perspective, for example, an array of lenses and apertures that partially collimates a light flux is considered a filter. "Surface-treated" can include changes in chemical composition, surface roughness, surface geometry, surface microfeatures, or multilayer interference coatings.

In some embodiments, the analyte detection system includes a microchannel-based optical filter device arranged between the implantable sensor and the optical detector, wherein the presently disclosed a microchannel-based optical filter device provides high optical rejection of high-AOI light with light throughput higher than alternative optical filter devices having the same degree of rejection. For example, the microchannel-based optical filter device includes a surface-treated microchannel. In one example, the surface treatment is an arrangement of grooves etched into the walls of the microchannel and wherein the grooves serve to partially or completely absorb, trap, and/or block high-AOI light. Further, the grooves are arranged substantially parallel to the axis of the microchannel. Further, the number, spacing, depth, width, and/or sidewall angles of the grooves may vary.

In some embodiments, the presently disclosed analyte detection system provides a microchannel-based optical filter device including a surface-treated microchannel that can reject excitation light at orders of magnitude greater than emission light power at the worst-case AOI of the system.

In some embodiments, the presently disclosed analyte detection system provides a microchannel-based optical filter device including a surface-treated microchannel that can reject a greater amount of high-AOI light as compared with conventional smooth-walled microchannels. In one example, the maximum acceptance angle of the microchannel-based optical filter device may be from about 11 degrees to about 24 degrees.

In some embodiments, the presently disclosed analyte detection system provides a microchannel-based optical filter device including a surface-treated microchannel supplying an optical detector.

In some embodiments, the presently disclosed analyte detection system provides a microchannel-based optical filter device including a surface-treated microchannel and one or more discrete optical devices, such as, but not limited to, a discrete optical bandpass filter and a discrete optical detector.

In some embodiments, the presently disclosed analyte detection system provides an integrated microchannel-based optical filter device including a surface-treated microchannel and one or more integrated optical devices, such as, but not limited to, an integrated optical bandpass filter and an integrated optical detector.

In some embodiments, the presently disclosed analyte detection system provides an integrated microchannel-based optical filter device including a surface-treated microchannel and one or more integrated optical devices that may be formed using large-scale manufacturing processes.

In some embodiments, the presently disclosed analyte detection system that includes an integrated microchannel-based optical filter device including a surface-treated microchannel may be implemented in a wearable detection device.

Further, a method of operation of the presently disclosed microchannel-based optical filter device including a surface-treated microchannel is provided with respect to the high optical rejection of high-AOI light.

Referring now to FIG. 1 is a block diagram of an example of the presently disclosed analyte detection system 100 including a microchannel-based optical filter device providing high optical rejection of high-AOI light. For example, the presently disclosed analyte detection system 100 and optical filter device can be used for reading an implantable sensor and determining an analyte value.

For example, analyte detection system 100 includes a detection device 110 that can be positioned with respect to an implantable sensor 150 implanted in tissue 105. For example, implantable sensor 150 may be implanted a few millimeters (e.g., 1-10 mm) under the skin of the user. Further, detection device 110 of analyte detection system 100 features an optical filter device 120 including a surface-treated microchannel wherein the surface-treated microchannel serves to absorb, trap, and/or block high-AOI light.

Implantable sensor 150 may be, for example, an analyte-sensing fluorescent sensor. When implanted in tissue 105, implantable sensor 150 is in good contact (close proximity) to blood vessels and has direct access to interstitial fluid. Implantable sensor 150 may include analyte-sensing dye. The analyte-sensing dye in implantable sensor 150 is an analyte-specific dye for targeting the analyte of interest. Examples of analytes of interest may include, but are not limited to, oxygen, reactive oxygen species, glucose, lactate, pyruvate, cortisol, creatinine, urea, sodium, magnesium, calcium, potassium, vasopressin, hormones (e.g., Luteinizing hormone), pH, $CO_2$, cytokines, chemokines, eicosanoids, insulin, leptins, small molecule drugs, ethanol, myoglobin, nucleic acids (RNAs, DNAs), fragments, polypeptides, single amino acids, and the like. In one example, implantable sensor 150 may be a glucose sensor, and therefore the analyte-sensing dye is a glucose-sensing dye.

Detection device 110 is an optical detection device that includes a microchannel-based optical filter device 120 that provides high optical rejection of high-AOI light. Detection device 110 further includes an excitation light source 140 that emits an excitation light 142, certain optical components 144, an optical detector 146, and a communications port 148. In some embodiments, detection device 110 may include a power source (not shown), such as a battery. Detection device 110 is designed to be fitted against the surface of the skin. Detection device 110 may be implemented using a printed circuit board (PCB), a flexible PCB, or other flexible substrate. Detection device 110 may be, for example, a wearable detection device (not shown) provided as a patch that can be placed on the surface of the skin (i.e., tissue 105) in close proximity to implantable sensor 150.

Excitation light source 140 is arranged to transmit excitation light 142 from the surface of the skin, through the tissue 105, and to implantable sensor 150. The excitation light 142 from excitation light source 140 is within the excitation wavelength range of any analyte-sensing dye of implantable sensor 150. Suitable excitation light sources may include, but are not limited to, lasers, semi-conductor lasers, light emitting diodes (LEDs), and organic LEDs. Optical components 144 may include any types of components (e.g., optical filters, lenses, apertures) needed in detection device 110 for conditioning excitation light source 140, including embodiments of microchannel-based optical filter device 120.

Optical detector 146 is arranged in relation to excitation light source 140, wherein optical detector 146 is used to detect emission light 152 that originates from the analyte-sensing dye of implantable sensor 150 and passes through tissue 105. For example, optical detector 146 detects emission light 152 in the emission wavelength of the analyte-sensing dye of implantable sensor 150. Suitable optical detectors may include, but are not limited to, photodiodes, complementary metal-oxide-semiconductor (CMOS) detectors, charge-coupled device (CCD) detectors, avalanche photodiodes, silicon photomultipliers, and digital cameras.

Optical detector 146 may be filtered using microchannel-based optical filter device 120 to measure the optical signals emitted within the desired wavelength ranges and wherein microchannel-based optical filter device 120 provides high optical rejection of high-AOI light as compared with conventional optical detection devices. For example, implantable sensor 150 is excited at its excitation wavelength via excitation light 142. Then, implantable sensor 150 absorbs the excitation light 142 and emits longer wavelength emission light 152. The tissue 105 also reflects a portion of the excitation light 142 back towards the optical filter device 120. A microchannel-based optical filter device 120 rejects the undesired wavelengths, including reflected excitation light 142, allowing for the emission light 152 to be measured accurately by optical detector 146. Microchannel-based optical filter device 120 may include, for example, an arrangement or stack of one or more optical components. More details of example of microchannel-based optical filter devices are shown and described hereinbelow with reference to FIG. 3 through FIG. 13.

Detection device 110 may include a built-in processor (not shown) and memory (not shown). In this example, the processing capability of analyte detection system 100 is on board detection device 110 that is configured to be located on the surface of the skin. In another example, the processing capability of analyte detection system 100 is external to detection device 110 that is located on the surface of the skin. Accordingly, in such an embodiment a communications port 148 can be provided between detection device 110 and a separate computing device 160, wherein computing device 160 may be used for processing any information from detection device 110. Computing device 160 may be any type of computing device, such as a desktop computer, a laptop computer, a tablet device, a mobile phone, a smartphone, a smartwatch, a centralized server or cloud computer, and the like. In this example, communications port 148 may facilitate a wired and/or wireless communications link from excitation light source 140 and/or optical detector 146 to, for example, computing device 160. For example, communications port 148 may be a wired communications port, such as a USB port, and/or a wireless communications port that uses, for example, WiFi and/or Bluetooth® technology.

Computing device 160 may use a desktop application 162 or mobile app 162 to process any information from implantable sensor 150. Namely, desktop application 162 or mobile app 162 may include any software and/or hardware components for processing any information from implantable sensor 150. While detection device 110 may include battery power, in other embodiments, computing device 160 supplies power to detection device 110.

In one example, computing device 160 may be used to activate excitation light source 140, wherein excitation light source 140 emits excitation light 142 and illuminates the analyte-sensing dye in implantable sensor 150, wherein the analyte-sensing dye has a certain absorption spectrum and a certain emission spectrum. Then, optical detector 146 collects emission light 152 from implantable sensor 150 that passes through microchannel-based optical filter device 120 and wherein microchannel-based optical filter device 120 provides high optical rejection of high-AOI light of emission light 152. Then, computing device 160 collects information from optical detector 146, wherein optical detector 146 converts optical signals received from implantable sensor 150 to an electrical signal output. The measured intensity of emission light 152 correlates to an analyte value. For example, in an implantable glucose sensor 150 the measured intensity of emission light 152 (i.e., fluorescence) correlates to the amount or concentration of glucose present.

Generally, excitation light 142 reflected by the tissue 105 is orders of magnitude stronger than emission light 152. Accordingly, microchannel-based optical filter device 120 is used to separate excitation light 142 and emission light 152. For example, microchannel-based optical filter device 120 is used to reject reflected excitation light 142 as much as possible so that emission light 152 only is measured by optical detector 146. The presently disclosed microchannel-based optical filter device 120 has a surface-treated microchannel. In one example, the surface treatment is an arrangement of grooves etched into the walls of the microchannel and wherein the grooves serve to absorb, trap, and/or block high-AOI light with greater effectiveness as compared with conventional smooth-walled microchannels. Accordingly, the presently disclosed microchannel-based optical filter device 120 may be used to transform a wide-angle light source into a narrower angle light source and thereby improve the angle-averaged wavelength cutoffs of multi-layer dielectric filters. More details of examples of the microchannel-based optical filter device 120 with the surface-treated microchannel are shown and described hereinbelow with reference to FIG. 3 through FIG. 13.

Referring now to FIG. 2 is a block diagram of detection device 110 of analyte detection system 100 and showing more details of the presently disclosed microchannel-based optical filter device 120. The optical power of a fluorophore excitation source is often orders of magnitude stronger than the resulting fluorescence emission. Therefore, it is beneficial for an optical filter used to separate the excitation light from the emission light to be designed to reject excitation light at orders of magnitude greater than emission light power at the power-averaged AOI of the system. For example, the cutoff wavelengths (or filter window) for optical band-pass filters are dependent on the AOI of the incident light. As AOI increases, the filter window shifts to shorter wavelengths (i.e., blue shifts). In the case of fluorophore excitation and emission, this blue shift causes the optical filter window for the emission to shift towards the excitation light source, making the filter less effective for high AOI light. Accordingly, microchannel-based optical filter device 120 of analyte detection system 100, which uses on intensity-based measurements, provides an optical filter that can reject excitation light at orders of magnitude greater than emission light power at the averaged over the AOI distribution of the system, mitigating the shift in the filter window.

FIG. 2 shows excitation light 142 striking implantable sensor 150. Additionally, both a certain amount of normal excitation light 142 and a certain amount of high angle excitation light 142 reaches microchannel-based optical filter device 120, for example by reflection or scattering from tissue 105. In response to excitation light 142, implantable sensor 150 produces emission light 152 that strikes at a range of AOIs to microchannel-based optical filter device 120. However, because microchannel-based optical filter device 120, in combination with an optical wavelength filtering device (see 145 in FIG. 12 and FIG. 13, and 214 in FIG. 15 and FIG. 16 for exemplary embodiments of microchannel-based optical filter device 120 combined with optical wavelength filters), is designed to reject excitation light at orders of magnitude greater than emission light power averaged over the AOI distribution of the system, microchannel-based optical filter device 120, in combination with an optical wavelength filtering device, substantially rejects both the normal excitation light 142 and the high angle excitation light 142 while at the same time transmitting emission light 152.

Again, microchannel-based optical filter device 120 has a surface-treated microchannel (e.g., a grooved-surface microchannel as shown in FIG. 3 through FIG. 13) that is able to absorb, trap, and/or block high-AOI light with greater effectiveness as compared with conventional smooth-walled microchannels. Accordingly, microchannel-based optical filter device 120 may be used to transform a wide-angle light source into a narrower angle light source and thereby improve the angle-averaged wavelength cutoffs of multilayer dielectric filters. In one example, the distribution of output angles emitted by microchannel-based optical filter device 120 may cut off at a value ranging from about +/−11 degrees to about +/−24 degrees.

FIG. 3 illustrates a full perspective view and FIG. 4A and FIG. 4B illustrate a cutaway perspective view of examples of a microchannel-based optical filter device including a surface-treated microchannel; FIG. 4A illustrates tapering of the microchannels, and FIG. 4B illustrates zero-tapering. For example, microchannel-based optical filter device 120 may include a filter body 122 that has a surface-treated microchannel 124 formed therein. Surface-treated microchannel 124 is a channel that runs along the length of filter body 122 and is parallel to the axis of filter body 122. In this example, the surface treatment of surface-treated microchannel 124 is in the form of an arrangement of grooves 126 that are provided around the wall of surface-treated microchannel 124 and wherein grooves 126 run parallel to the axis of filter body 122. Further, each end of microchannel-based optical filter device 120 has a filter face 128.

Microchannel-based optical filter device 120 may be, for example, from about 0.25 mm to about 2 mm long and have a width, height, or diameter from about 2 mm to about 8 mm. Filter body 122 may be formed of any material suitable for the fabrication of a microchannel 124. For example, filter body 122 may be formed of silicon, GaAs, glass, ceramic, or polymers. Further, the outside diameter of surface-treated microchannel 124 may be, for example, from about 0.1 mm to about 0.6 mm. The aspect ratio L/D of the length to the outside diameter, for example for output angle distributions with a cutoff between +/−11 deg and +/−24 deg, can be between 2 and 30. For certain common etching and coating processes in silicon, L/D can be 5 to 10. Note that by stacking N discrete layers with aspect ratio L/D, it's possible to create a multilayer assembly with aspect ratio N*L/D.

Grooves 126 provide deep, high-slope features in the sidewalls of surface-treated microchannel 124 to increase the number of reflections from the sidewalls, thereby decreasing net light transmission of reflected rays at constant reflectivity. Other surface treatments such as Black Chrome or Acktar LithoBlack can decrease the reflectivity of a single reflection. For even lower net transmission, the grooves 126 can be coated with Black Chrome or Acktar LithoBlack. Surface-treated microchannel 124 may include any number of grooves 126 that may be spaced radially substantially evenly or unevenly around the wall of surface-treated microchannel 124. Further, the number, spacing, depth, width, and/or sidewall angles of grooves 126 may vary. For example, FIG. 5 shows a plan view of an example of a surface treatment groove pattern 130 for forming the surface-treated microchannel 124 of the microchannel-based optical device 120 shown in FIG. 3, FIG. 4A, and FIG. 4B.

Surface treatment groove pattern 130 provides a "flower" or "gear" type of pattern. In this example, surface treatment groove pattern 130 includes twenty outer points 132, twenty inner points 134, and the sidewalls 136 therebetween. One outer point 132 and its two inner points 134 correspond to one groove 126 of surface-treated microchannel 124. Each outer point 132 may have a flattened surface (e.g., flatten surface from about 5 μm to about 50 μm wide, depending on the outer diameter of the microchannel). By contrast, each inner point 134 may come substantially to a point. However, this is exemplary only. Outer points 132 and/or inner points 134 may be flattened, rounded, pointed, or any combinations thereof. In this example, the outside diameter of surface treatment groove pattern 130 may be about 0.2 mm and the inside diameter may be about 0.13 mm. Accordingly, in this example, the angle of sidewalls 136 may be about 70 degrees. Thus, according to some embodiments, each groove can have a depth (at at least one end surface) of 0.05-0.15 mm, and the angle of the sidewalls can be between 60 and 75 degrees.

Using, for example, surface treatment groove pattern 130, one way to form surface-treated microchannel 124 in filter body 122 (e.g., silicon) is by an etching process. However, an inherent problem of etching fine features, such as grooves 126, is that the deeper the etch the less defined the features become. That is, a certain depth may be reached in the etching process wherein grooves 126 may diminish or substantially disappear (see sidewalls 136'). Accordingly, a balance should be achieved with respect to the length of microchannel-based optical filter device 120 and its operability.

Further, because of this inherent etching characteristic, the etch ending end of surface-treated microchannel 124 may have a larger diameter (i.e., opening) than the etch beginning end of surface-treated microchannel 124. That is, surface-treated microchannel 124 may have a slight cone or tapered shape. An example of this is shown in FIG. 4A. In this case, in analyte detection system 100, the larger end of surface-treated microchannel 124 should be oriented toward implantable sensor 150 while the smaller end of surface-treated microchannel 124 should be oriented toward optical detector 146. One way to mitigate this inherent etching characteristic is to limit the etching depth (i.e., the length of microchannel-based optical filter device 120) and provide a stack of multiple microchannel-based optical filter devices 120.

Referring now to FIG. 6 and FIG. 7 is a full perspective view and a cutaway perspective view, respectively, of another example of microchannel-based optical filter device 120 including surface-treated microchannel 124. Microchannel-based optical filter device 120 shown in FIG. 6 and FIG. 7 is similar to the microchannel-based optical filter device 120 shown in FIG. 3, FIG. 4A, and FIG. 4B except that surface-treated microchannel 124 is a slightly different pattern. For example, FIG. 8 shows a plan view of another example of surface treatment groove pattern 130 for forming the surface-treated microchannel 124 of the microchannel-based optical filter device 120.

In this example, surface treatment groove pattern 130 includes ten outer points 132, ten inner points 134, and the sidewalls 136 therebetween. Again, one outer point 132 and its two inner points 134 correspond to one groove 126 of surface-treated microchannel 124. Again, outer points 132 and/or inner points 134 may be flattened, rounded, pointed, or any combinations thereof. In this example, the outside diameter of surface treatment groove pattern 130 may be about 0.26 mm and the inside diameter may be about 0.12 mm. Accordingly, in this example, the angle of sidewalls 136 may be about 80 degrees.

Further to the example, FIG. 9 and FIG. 10 show yet other examples of surface treatment groove patterns 130 for forming surface-treated microchannel 124 of microchannel-based optical filter device 120.

Referring now to FIG. 11 is a block diagram of an example of microchannel-based optical filter device 120, according to an embodiment. In this example, light passing through the microchannel-based optical filter device 120 illuminates the optical detector 146, which may be, for example, a discrete optical detector device. A certain amount of excitation light 142 and/or emission light 152 may enter surface-treated microchannel 124 of microchannel-based optical filter device 120, certain components of which may be wide-angle or high-AOI light. Wide-angle or high-AOI light strikes grooves 126 of surface-treated microchannel 124. In so doing, a certain amount of the undesired wide-angle or high-AOI light may be absorbed, trapped, and/or blocked by grooves 126. That is, any wide-angle or high-AOI light entering surface-treated microchannel 124 will take multiple reflections or bounces off of grooves 126. With each reflection or bounce off of grooves 126, the intensity of the undesired wide-angle or high-AOI light diminishes.

Accordingly, the presence of grooves 126 causes a high amount of wide-angle or high-AOI light to be blocked from exiting surface-treated microchannel 124 of microchannel-based optical filter device 120. Accordingly, microchannel-based optical filter device 120 may be used to absorb, trap, and/or block high-AOI light with greater effectiveness as compared with conventional smooth-walled microchannels having the same aspect ratio length/diameter. For example, for each additional reflection due to microgrooves, in the example where the filter body is silicon and with no additional coating, the transmission of the ray as compared with conventional smooth-walled microchannels may be, for example, can be lower by a factor of 0.4 to 0.9. For a distribution of high-AOI rays having a range of numbers of additional reflections, the net transmitted power is a complex function of the microchannel properties. With a silicon filter body and no coating on the microgrooves, the angle-averaged transmission outside a desired cutoff angle, for ex+/−20 deg, can by 75% to about 25% of the comparable transmission of conventional smooth-walled microchannels having the same light transmission for desired light inside the same cutoff angle. With added coatings on the microchannel grooves, the net transmission of high-angle light can be further reduced.

Microchannel-based optical filter device 120 may be used to transform a wide-angle light source into a narrower angle light source and thereby improve the angle-averaged wavelength cutoffs of multilayer dielectric filters. That is, microchannel-based optical filter device 120, in combination with an optical wavelength filtering device (see 145 in FIGS. 12 and 13, and 214 in FIGS. 15 and 16 for exemplary embodiments of microchannel-based optical filter device 120 combined with optical wavelength filters), is designed to transmit the desired in-bandpass wavelengths at narrow angles to optical detector 146.

Referring now to FIG. 12 is a block diagram of another example of microchannel-based optical filter device 120 including other discrete optical components. In this example, microchannel-based optical filter device 120 supplies a discrete optical filter 145 followed by a discrete optical detector 146.

Discrete optical filter 145 may be, for example, a thin film optical bandpass filter. In this example, there may be risk of a certain amount to light exiting surface-treated microchannel 124 to be reflected back from discrete optical filter 145 and onto filter face 128 of microchannel-based optical filter device 120. That is, undesired out-of-bandpass light reflected at narrow angles by discrete optical filter 145 may reflect off filter face 128 into larger-angle light that then transmits through discrete optical filter 145 and reaches discrete optical detector 146. To mitigate this, an anti-reflection coating 147 may be provided on filter face 128 of microchannel-based optical filter device 120 to suppress the reflections. In another example, etched microstructures (not shown) may be provided on filter face 128 to suppress the reflections. In yet another example, both anti-reflection coating 147 and etched microstructures (not shown) may be provided on filter face 128 to suppress the reflections. Anti-reflection coating 147 may be, for example, a dark or "Black Chrome" coating, an Acktar black coating (e.g., Acktar's Litho Black™) a black silicon (b-Si) coating, carbon nanotubes, and the like.

Referring now to FIG. 13 is a block diagram of an example of an integrated microchannel-based optical filter device 120 including other integrated optical components. For example, an integrated microchannel-based optical filter device 120 may be provided wherein microchannel-based optical filter device 120 includes an integrated optical filter 145 and an integrated optical detector 146. In this example, a thin integrated optical filter 145 may be used in place of an anti-reflection mechanisms at filter face 128 as shown in FIG. 12. For example, the undesired out-of-bandpass wavelength reflected by integrated optical filter 145 at narrow angles may be transmitted back into surface-treated microchannel 124 and absorbed.

Referring now to FIG. 11, FIG. 12, and FIG. 13, in one example, the cutoff angle (for example the 50% transmission point) in the transmission vs. angle curve of microchannel-based optical filter device 120 may be from about +/−11 degrees to about +/−24 degrees.

Manufacturing microchannel-based optical filter device 120 with discrete optical components, such as discrete optical filter 145 and discrete optical detector 146 (see FIG. 12) may be more costly than integrated microchannel-based optical filter device 120 including integrated optical filter 145 and integrated optical detector 146, as shown in FIGS. 14-16, which may be more easily formed using a large-scale manufacturing process.

Referring now to FIG. 14 is a plan view of an example of a microchannel-etched wafer 200 for supporting the large-scale manufacturing process of microchannel-based optical filter devices 120. Further, FIG. 15 shows a cross-sectional view of a portion of microchannel-etched wafer 200 taken along line A-A of FIG. 14. In this example, microchannel-etched wafer 200 includes a substrate 210, which may be, for example, a 3-inch, 4-inch, 6-inch, or 12-inch diameter silicon wafer.

In microchannel-etched wafer 200, surface-treated microchannels 124 may be etched into substrate 210 at the multiple die locations. Common etch processes used in microfabrication may include, but are not limited to, wet etch processes, dry etch processes, plasma etch processes, and the like. Specific etching processes include, for example, reactive-ion etching (RIE) and deep reactive-ion etching (DRIE).

Following the etching process to form surface-treated microchannels 124, an anti-reflection layer 212 may be deposited atop substrate 210, then an optical filter layer 214 may be deposited atop anti-reflection layer 212, then an optical detector layer 216 may be deposited atop optical filter layer 214. In one example, anti-reflection layer 212 may be formed of, for example, a dark or "Black Chrome" coating, an Acktar black coating (e.g., Acktar's Litho Black™), a black silicon (b-Si) coating, carbon nanotubes, and the like. In one example, optical filter layer 214 may be formed of stacks of high and low refractive-index material that is from about 5 μm to about 50 μm thick. The optical filter layer 214 may also be a glass substrate 0.25 to 1.5 mm thick with multilayer dielectric stacks 5 to 50 um thick on each side. In one example, optical detector layer 216 may be formed of silicon.

In one example, substrate 210 may be about 0.5 mm thick, the outside diameters of surface-treated microchannels 124 may be about 180 μm on 500 μm centers, and microchannel-etched wafer 200 may be diced into devices that may be from about 2 mm square to about 8 mm square.

Using microchannel-etched wafer 200, a large-scale manufacturing process is provided by which the presently disclosed microchannel-based optical filter devices 120 may be mass produced and packaged. For example, FIG. 16 shows a perspective view of a block or array of microchannel-based optical filter devices 120 that may be diced from the microchannel-etched wafer 200 shown in FIG. 14 and FIG. 15. The large-scale manufacturing process may be, for example, a wafer-scale manufacturing process, a platter-scale manufacturing process, a roll-to-roll laser die cutting process, and the like. The resulting diced assemblies can then be die-bonded and assembled into packages, for example SMT packages, that can be further assembled via standard techniques onto printed circuit boards (PCBs), as is well-known in semiconductor device manufacturing. Once fabricated and packaged, individual microchannel-based optical filter devices 120 may be shipped as drop-in modules to be installed in any types of systems that use optical detection, such as analyte detection system 100 shown in FIG. 1. Microchannel-etched wafer 200 is one example of a large-scale manufacturing process wherein a wafer is provided that includes row and columns of devices. Microchannel-etched wafer 200 is processed and then diced into individual microchannel-based optical filter devices 120.

An example of the general steps for processing microchannel-etched wafer 200 may include, but is not limited to, (1) pattern and etch the silicon wafer holes; (2) coat the etched wafer with low-reflectivity coating; (3) bond glass wafers coated with filters to one or both sides of low-reflectivity-coated silicon wafers (e.g., filter side against coated silicon wafer, protects dielectric and low-reflectivity coatings); and (4) dice wafer. The filter wafer can be bonded to a wafer containing detectors before dicing or, after dicing, individual microchannel-based optical filter devices can be bonded to individual detectors.

FIG. 17 illustrates a series of cross-sections at different etching depths of an example of a surface-treated microchannel model 170 and indicating the etching characteristics of surface-treated microchannel 124 of microchannel-based optical filter device 120. Surface-treated microchannel model 170 shows that a certain etching depth may be reached wherein grooves 126 may diminish or substantially disappear. Profile 171 depicts a cross section of the microchannel at the etch-beginning end of the microchannel. Profile 172 depicts a cross section of the microchannel at a midpoint of the microchannel. Profile 173 depicts a cross section of the microchannel at an etch ending surface of the microchannel. Accordingly, the etch ending end of surface-treated microchannel 124 may have a larger diameter (i.e., opening) than the etch beginning end of surface-treated microchannel 124. That is, surface-treated microchannel 124 may have a slight cone or tapered shape. When assembled into a detection device, typically the etch ending end (the end with the larger diameter) would be configured to be disposed adjacent the skin and the etch beginning end would be disposed adjacent the detector. In some instances, however, the end of the microchannel-based optical filter device having the larger diameter may be disposed adjacent the detector.

FIG. 18 illustrates a flow diagram of an example of a method 300 of operation of microchannel-based optical filter device 120 of the presently disclosed analyte detection system 100. For example, method 300 indicates the operation of microchannel-based optical filter device 120 including surface-treated microchannel 124 with respect to providing high optical rejection of high-AOI light. Method 300 may include, but is not limited to, the following steps.

At a step 310, the microchannel-based optical filter device 120 that includes surface-treated microchannel 124 is provided. In one example, microchannel-based optical filter device 120 shown in FIG. 11 is provided. In another example, microchannel-based optical filter device 120 shown in FIG. 12 is provided. In yet another example, the integrated microchannel-based optical filter device 120 shown in FIG. 13 is provided.

At a step 315, microchannel-based optical filter device 120 is placed in proximity to light to be detected. For example and referring now again to FIG. 1 and FIG. 2, microchannel-based optical filter device 120 is placed in proximity to tissue 105 from which is emitted emission light 152 from implantable sensor 150.

At a step 320, the high-AOI light strikes the grooved walls of microchannel-based optical filter device 120, while narrower angle light passes through microchannel-based optical filter device 120. For example and referring now again to FIG. 11, FIG. 12, and FIG. 13, the high-AOI light strikes grooves 126 of surface-treated microchannel 124 of microchannel-based optical filter device 120. At the same time, the narrower angle light does not strike grooves 126, or strikes the grooves 126 fewer times, and therefore passes through microchannel-based optical filter device 120 with higher transmission efficiency than the high-AOI.

At a step 325, the high-AOI light reflects multiple times along the grooved walls of microchannel-based optical filter device 120 and the intensity diminishes with each reflection. For example and referring still to FIG. 11, FIG. 12, and FIG.

13, the high-AOI light reflects multiple times along grooves 126 of surface-treated microchannel 124 of microchannel-based optical filter device 120 and with each reflection or bounce the intensity of the high-AOI light diminishes.

At a step 330, the high-AOI light is substantially blocked from reaching output end of microchannel-based optical filter device 120 that includes surface-treated microchannel 124. As described herein, light is substantially blocked when, for every 10^6 photons having an AOI greater than the acceptance angle, 1 or fewer photons passes the microchannel-based optical filter device (≥OD6 rejection). For example and referring still to FIG. 11, FIG. 12, and FIG. 13, because of the high-AOI light absorbing, trapping, and/or blocking action of grooves 126 of surface-treated microchannel 124 in microchannel-based optical filter device 120, the high-AOI light is substantially blocked from reaching the output end of microchannel-based optical filter device 120. In one example, the maximum acceptance angle of microchannel-based optical filter device 120 may be from about 11 degrees to about 24 degrees.

In summary and referring now again to FIG. 1 through FIG. 18, the presently disclosed analyte detection system 100, microchannel-based optical filter device 120, and method 300 provides for improved optical rejection of high-AOI light. For example, the optical detector portion (e.g., detection device 110) of analyte detection system 100 features microchannel-based optical filter device 120 with surface-treated microchannel 124 wherein surface-treated microchannel 124 serves to absorb, trap, and/or block high-AOI light. In one example, the surface treatment is an arrangement of grooves 126 etched into the walls of surface-treated microchannel 124 and wherein grooves 126 serve to absorb, trap, and/or block high-AOI light. Further, grooves 126 are arranged substantially parallel to the axis of surface-treated microchannel 124. Further, the number, spacing, depth, width, and/or sidewall angles of grooves 126 may vary.

The presently disclosed analyte detection system 100 provides microchannel-based optical filter device 120 with surface-treated microchannel 124 that can reject excitation light at orders of magnitude greater than emission light power at the worst-case AOI of the system. Further, microchannel-based optical filter device 120 with surface-treated microchannel 124 can reject a greater amount of high-AOI light as compared with conventional smooth-walled microchannels having a width and length that provide similar transmission of low-AOI light. In one example, an angular cutoff parameter, for example the half-max points of the transmission vs. angle curve, of microchannel-based optical filter device 120 may be from about +/−11 degrees to about +/−24 degrees.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. An apparatus, comprising:
a light source configured to illuminate a sensor implanted within tissue;
an optical filter body defining a microchannel, the microchannel running through a length of the filter body defining an axis, a surface at an interface of the optical filter body and microchannel having a plurality of grooves running parallel to the axis of the microchannel,
the optical filter body and the microchannel collectively configured to selectively reject light having an angle of incidence greater than a predetermined threshold; and
a detector configured to receive emission light from the sensor that has passed through at least one of the optical filter body or the microchannel in response to the sensor being illuminated by the light source.

2. The apparatus of claim 1, wherein the microchannel is from a plurality of microchannels defined by the optical filter body.

3. The apparatus of claim 1, wherein the plurality of grooves includes at least ten grooves.

4. The apparatus of claim 1, wherein each groove from the plurality of grooves has a depth of less than 0.15 mm.

5. The apparatus of claim 1, wherein each groove from the plurality of grooves is coated with an anti-reflective coating.

6. The apparatus of claim 1, wherein:
the light source is configured to illuminate the sensor with excitation light such that the sensor produces the emission light; and the optical filter body and the microchannel are collectively configured to selectively reject excitation light scattered by the tissue.

7. An apparatus, comprising:

an optical filter body defining a microchannel, the microchannel running through a length of the filter body from a first side of the optical filter body to a second side of the optical filter body, the microchannel defining an axis, a surface at an interface of the optical filter body and microchannel having a plurality of grooves running parallel to the axis of the microchannel, each groove from the plurality of grooves having a first depth at the first side of the optical filter body that is different from a second depth at the second side of the optical filter body.

8. An apparatus, comprising:

an optical filter body defining a microchannel, the microchannel running through a length of the filter body defining an axis, a surface at an interface of the optical filter body and microchannel having a plurality of grooves running parallel to the axis of the microchannel, each groove from the plurality of grooves has a depth of greater than 0.05 mm at a first end portion of the microchannel.

9. An apparatus, comprising:

a light source configured to illuminate a sensor implanted within tissue with excitation light;

an optical filter body defining a microchannel, the microchannel running through a length of the filter body defining an axis, a surface at an interface of the optical filter body and microchannel having a plurality of grooves running parallel to the axis of the microchannel;

a detector configured to receive emission light from the sensor in response to the sensor being illuminated by the light source; and an optical filter configured to selectively reject excitation light based on wavelength, the optical filter body and the microchannel collectively configured to selectively reject excitation light scattered by the tissue such that high angle of incidence excitation light does not reach the optical filter.

* * * * *